United States Patent [19]

Rosenthal et al.

[11] Patent Number: 5,028,787
[45] Date of Patent: Jul. 2, 1991

[54] NON-INVASIVE MEASUREMENT OF BLOOD GLUCOSE

[75] Inventors: Robert D. Rosenthal, Gaithersburg; Lynn N. Paynter, Elkridge; Linda H. Mackie, Rockville, all of Md.

[73] Assignee: Futrex, Inc., Gaithersburg, Md.

[21] Appl. No.: 298,904

[22] Filed: Jan. 19, 1989

[51] Int. Cl.$^5$ ............................................. G01N 21/35
[52] U.S. Cl. ..................................... 250/341; 250/339; 250/343
[58] Field of Search ................... 250/339, 341, 343; 356/39; 128/633

[56] References Cited

U.S. PATENT DOCUMENTS

| | | |
|---|---|---|
| 3,154,625 | 10/1964 | Kail . |
| 3,344,702 | 10/1967 | Wood et al. . |
| 3,396,280 | 8/1968 | Knudsen . |
| 3,463,142 | 9/1969 | Harte . |
| 3,638,648 | 2/1972 | Shaw . |
| 3,734,631 | 5/1973 | Justice et al. . |
| 3,776,642 | 12/1973 | Anson et al. . |
| 3,861,788 | 1/1975 | Webster . |
| 3,877,818 | 4/1975 | Button et al. . |
| 3,910,701 | 10/1975 | Henderson et al. . |
| 3,958,560 | 5/1976 | March . |
| 4,029,420 | 6/1977 | Simms . |
| 4,037,970 | 7/1977 | Webster et al. . |
| 4,095,105 | 6/1978 | Rosenthal . |
| 4,171,909 | 10/1979 | Kramer et al. . |
| 4,193,116 | 3/1980 | Funk . |
| 4,207,466 | 6/1980 | Drage et al. . |
| 4,226,540 | 10/1980 | Barten et al. . |
| 4,247,773 | 1/1981 | Nexo et al. . |
| 4,281,248 | 7/1981 | Fabinski et al. . |
| 4,286,327 | 8/1981 | Rosenthal et al. . |
| 4,310,763 | 1/1982 | Shields . |
| 4,341,473 | 7/1982 | Mast . |
| 4,379,233 | 4/1983 | Rosenthal . |
| 4,380,240 | 4/1983 | Jobsis et al. . |
| 4,404,642 | 9/1983 | Rosenthal . |
| 4,436,207 | 4/1984 | Klukis . |
| 4,439,037 | 3/1984 | Northeved et al. . |
| 4,442,844 | 4/1984 | Navach . |
| 4,447,725 | 5/1984 | Biggs et al. . |
| 4,466,076 | 8/1984 | Rosenthal . |
| 4,480,706 | 11/1984 | Rosenthal . |
| 4,484,819 | 11/1984 | Ulrich . |
| 4,487,278 | 12/1984 | Rosenthal . |
| 4,510,938 | 4/1985 | Jobsis et al. . |
| 4,515,165 | 5/1985 | Carroll . |
| 4,570,638 | 2/1986 | Stoddart et al. . |
| 4,608,990 | 9/1986 | Elings . |
| 4,621,643 | 11/1986 | New, Jr. et al. . |
| 4,627,008 | 12/1986 | Rosenthal . |
| 4,633,087 | 12/1986 | Rosenthal et al. . |
| 4,692,620 | 9/1987 | Rosenthal . |
| 4,734,584 | 3/1988 | Rosenthal . |
| 4,761,552 | 8/1988 | Rosenthal . |
| 4,768,516 | 9/1988 | Stoddard et al. . |
| 4,798,955 | 1/1989 | Rosenthal . |
| 4,801,804 | 1/1989 | Rosenthal . |
| 4,863,530 | 5/1987 | Shields . |
| 4,882,492 | 11/1989 | Schlager ........................... 250/346 |

FOREIGN PATENT DOCUMENTS

| | | |
|---|---|---|
| 160768 | 11/1985 | European Pat. Off. . |
| 1498616 | of 0000 | Fed. Rep. of Germany . |
| 3541165 | 5/1987 | Fed. Rep. of Germany ...... 128/633 |
| 401892 | of 0000 | U.S.S.R. . |
| 823832 | 11/1959 | United Kingdom . |

OTHER PUBLICATIONS

Conway et al., The Americal Journal of Clinical Nutrition, vol. 40 1123-1130, 1984.
Conway, J. M. et al., "In Vivo Body Composition Studies". Proc. Inst. Sci. Med., Eds Ellis, K. J. et al., Ch. 25, pp. 163-170.

(List continued on next page.)

Primary Examiner—Janice A. Howell
Assistant Examiner—Richard Hanig
Attorney, Agent, or Firm—Bernard, Rothwell, Brown

[57] ABSTRACT

A near-infrared quantitative analysis instrument and method non-invasively measures blood glucose by analyzing near-infrared energy following interactance with venous or arterial blood, or transmission through a blood containing body part. The instrument and method is accurate and can readily be utilized for at-home testing by diabetics.

32 Claims, 10 Drawing Sheets

OTHER PUBLICATIONS

Yelderman, M. et. al., "Evaluation of Pulse Oximetry", Anesthesiology, vol. 59, No. 4, pp. 349-352 (1983).

The Final Report of the Plausibility Study Performed by Trebor Industries for the California Growers Exchange.

Smoker, J. M. et al., "A Protocol to Assess Oxygen Therapy", Respiratory Care, vol. 31, No. 1, pp. 35-39 (1986).

Rosenthal, R. D., "Characteristics of Non-Destructive Near-Infrared Instruments for Grain and Food Products". Presented at the 1985 meeting of Japan Food Science.

Rosenthal, Robert D., "An Introduction to Near-Infrared Quantitative Analysis", 1977 Annual meeting of Americal Association of Cereal Chemists.

Massie, D. R., "Pat Measurement of Ground Beef with a Gallium Arsenide Infrared Emitter", ASAE Publication 1-76 (1976).

Mindel, B. D. "Infratec New Generation of Grain Analyzers". Agritrade pp. 30-32 (Jun. 1987).

Pacific Scientific Brochure. "Model 101 Cereal Grain Analyzer", Feb. 1982.

Dickey-John Corporation Brochure. "The Application-Matched Family of NIR Analyzers".

Technician Instr. Corp. Brochure. "The Analytical Laboratory of the Future . . . Today".

Rosenthal, R. D., "The Trebor-70 and the Trebor-7700. A New Generation in Near-IR Quantitative Measurement Systems". Presented at the 1985 meeting of Nellcor Corp. Brochures. "Ne-lcor Redefines Pulse Oximetry,, The Nellcor N-1000 Multi-Function Monitor", and The Nellcor Sensor Advantage.

Nellcor Corp. Pulse Oximetry, Note Nos. 1, 4, and 5.

NON-INVASIVE MEASUREMENT OF BLOOD GLUCOSE

FIELD OF THE INVENTION

This invention relates to instruments and methods for the non-invasive quantitative measurement of blood glucose.

BACKGROUND OF THE INVENTION

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

The normal method of determining blood chemistry is by removing a sample of blood (e.g. 5–10 ml) and performing one or more standard chemical tests. These types of tests are moderately expensive, require one class of trained technicians to remove the blood and another class of trained technicians to perform the chemical tests. Moreover, the results of the blood tests often are not available for several hours, and sometimes even several days.

Recently, an alternative type of technology (i.e. self-contained instruments) has been introduced for relatively rapid blood screening of a large number of subjects. These instruments, in general, use a much smaller blood sample (approximately 0.25 ml) from a "finger poke." This small blood sample is placed on a chemically-treated carrier and entered into the instrument. These instruments normally provide either an individual analysis (e.g. glucose level) or multiple analyses in a few moments. These types of instruments unfortunately are quite costly, e.g., in the range of several thousand dollars.

A third class of blood instrumentation is available for the specific purpose of determining glucose level in people with diabetes. This technology also uses a small sample from a finger poke and the sample is placed on a chemically treated carrier which is inserted into a portable battery operated instrument. In general, these instruments provide a single function; i.e. measurement of glucose. Although these specialized instruments are relatively low cost ($300 or less is typical), the cost of the disposable carrier "stick" must be considered. Since some diabetic patients may require glucose analysis four or more times a day, the cost over a period of a year can become significant.

Current glucose analytical systems require blood to be extracted from the body prior to performing the analysis. This blood withdrawal requirement limits the application of such testing; many people who may be interested in knowing their glucose level are reluctant to have either their finger poked or blood samples removed by hypodermic needle. This reluctance or anxiety in allowing blood sample removal is due to concern over the possibility of infection, discomfort (pain) and generalized patient fear.

Thus, there is a great need for non-invasive analytical instruments and methods that would provide essentially the same accuracy as conventional blood glucose tests. Moreover, there is a need for a non-invasive low-cost method for measurement of glucose in diabetic patients.

Near-infrared (sometimes referred to herein as simply "near-IR") quantitative analysis is widely used in the field of agriculture for determining chemical compositions within grain, oilseeds, and other agricultural products. As an example, near-IR energy reflected from the surface of finely ground seeds and grain provides information concerning protein and moisture content For a general introduction to near infrared quantitative analysis, see "An Introduction to Near-Infrared Quantitative Analysis" presented by Robert D. Rosenthal at the 1977 Annual Meeting of American Association of Cereal Chemists Near-infrared technology has been extended to allow totally non-destructive measurements by using light transmission through a sample as discussed in "Characteristics of Non-Destructive Near-Infrared Instruments for Grain and Food Products" by Robert D. Rosenthal, presented at the 1986 Meeting at the Japan Food Science Institute. Although this transmission approach avoids the need to finely grind the sample, it is not suited for use where access to two opposite surfaces is not available One example of this transmission approach is provided in U.S. Pat. No. 4,621,643 (New, Jr. et al., 1986) relates to an optical oximeter apparatus for determining pulse rate and degree of arterial oxygen saturation. Light energy is passed through an appendage of the body, e.g. a finger, and strikes a detector positioned on a side of the appendage opposite from the light source. Pulse rate and saturated oxygen are calculated from coefficients of extinction of light at the selected wavelengths.

Another approach to near-infrared quantitative analysis, using near-infrared interactance, was developed for non-invasively measuring body fat content. This approach is described in "A New Approach for the Estimation of Body Composition: Infrared Interactance", Joan M. Conway et al., The American Journal of Clinical Nutrition, 40: Dec. 1984, pages 1123–1230. In this non-invasive technique, a small optical probe that allows optical energy to enter the arm is placed on the biceps. The percent body fat of the entire body is determined by measuring the spectrum change of the energy returned from an area adjacent the light entry point.

SUMMARY OF THE INVENTION

In accordance with the present invention, a near-infrared quantitative analysis instrument for measuring blood glucose comprises means for introducing near-IR energy into blood present in a body part of a subject, means for detecting near-IR energy emerging from the subject, means for converting a signal corresponding to the detected energy into a readout indicative of the quantity of glucose present in the blood of the subject, and means for positioning the introducing means and detecting means adjacent to the body part of the subject.

The present invention also provides methods for the near-infrared quantitative analysis of blood glucose, these methods including the steps of introducing near-IR energy into the blood within a body part of a subject, detecting near-IR energy emerging from the subject, the detector providing a signal upon detecting said emerged energy, and processing the signal to provide a second signal indicative of the amount of glucose present in the blood. Some of these inventive methods utilize the principal of near-IR transmission while others utilize the principal of near-IR interactance.

In accordance with one aspect of the present invention, a near-infrared quantitative analysis instrument for measuring blood glucose comprises means for introducing near-IR energy into blood present in a blood vessel, means for detecting near-IR energy following interactance of the same with the blood, and means for positioning the introducing means and detecting means over a blood vessel of the subject.

This aspect of the invention further relates to methods wherein near-IR energy is introduced into a vein or artery of a subject and interacts with blood glucose, the near-IR energy emerging from the subject is detected by a detector which provides an electrical signal, and the signal is processed to provide a readout indicative of the amount of glucose in the blood.

This aspect of the invention also relates to means and methods for marking a position over a vein or artery of a subject and then aligning a near-IR analysis instrument with the markings to accurately position the instrument.

Another aspect of the invention relates to an apparatus for measuring blood glucose via near-IR transmission through a blood-containing body part, the apparatus including means for introducing near-IR energy into one side of a body part, means for detecting near-IR energy emerging from an opposite side of the body part and means for positioning the near-IR introducing and detecting means on opposite sides of the body part.

This aspect of the invention also relates to methods for measuring blood glucose via near-IR transmission including the steps of introducing near-IR energy into one side of a blood-containing body part, detecting near-IR energy emerging from an opposite side of the body part and calculating blood glucose content.

DETAILED DESCRIPTION OF THE PREFERRED EMBODIMENTS

Figure 1:
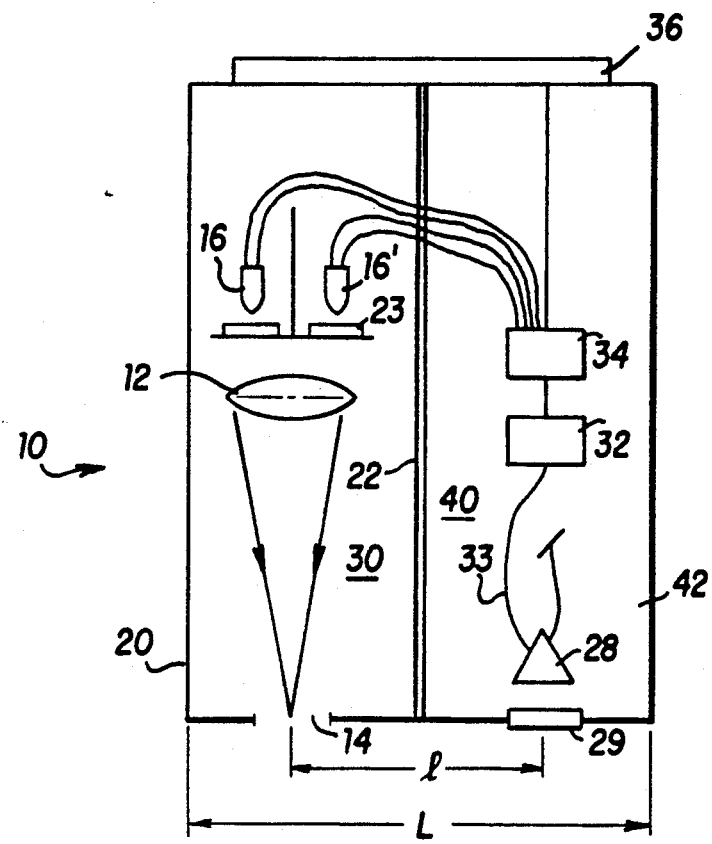
FIG. 1 is a partially schematic elevational view of a near-infrared quantitative blood analysis instrument to which the present invention pertains.

In accordance with one embodiment, the invention uses the principle of light interactance to measure blood glucose level non-invasively by locating an optical transmitter and a detector on the skin surface near either an artery or vein. Alternatively, the invention uses the principal of light transmission through a portion of the body that has relatively uniform profusion of blood in order to measure non-invasively blood glucose.

In general, the arteries and veins of the human body are buried deep in the body to protect them from possible harm. However, in certain locations of the body, these blood carrying vessels are close to the skin surface. This is particularly true for veins. Some examples of such locations are at the crease of the elbow, the wrist, the back of the hand, and the bridge of the nose. Since the concentration of glucose is relatively constant in both the veins and arteries, valid measurements can be obtained in either. However, because veins are generally closer to the skin's surface, they usually are the better candidate for non-invasive measurements.

The finger tip is another site particularly well suited for performing blood measurements with near-IR light. The blood supply is distributed within the finger tip and, thus, small variations in the placement of a near-IR emitter or detector will not have a profound effect on the measurement results.

According to one embodiment of the invention utilizing near-IR interactance analysis techniques, near-IR light energy at bandwidths centering on one or more wavelengths of interest is passed through the skin and connective tissues and into a blood vessel of a subject. A portion of the energy re-emerges from the blood vessel of the test subject and is detected by a detector. Following amplification of the detector-generated signal, the amplified output is processed into an output signal indicating the amount of glucose in the subject's blood. The output signal drives a display device for providing a visual display of blood glucose content.

According to another embodiment of the invention utilizing near-IR transmission analysis techniques, near-IR light energy at bandwidths centering on one or more wavelengths of interest is transmitted through a blood-containing portion of the body of a test subject. The near-IR energy emerges from the test subject, generally opposite the near-IR source, and is detected by a detector. Following amplification of the detector-generated signal, the amplified output is processed into an output signal indicating the amount of glucose in the subject's blood.

In one embodiment utilizing near-IR interactance, the entire analytical instrument, including near-infrared source, transmitter, detector, amplifier, data processing circuitry and readout is contained within a lightweight hand-held unit. See FIG. 1. Infrared emitting diodes (IREDs) disposed in one chamber of the unit are focused to transmit near-IR energy of preselected wavelength(s) to, e.g., a prominent vein of the wrist. The near-IR energy interacts with the constituents of the venous blood and is re-emitted from the vein. A detector housed within a second chamber of the unit is disposed along the vein a distance (l) from the emitter and collects this energy. The detected signal is amplified and data processed into a signal indicative of the amount of glucose in the blood. This signal is then fed to a readout device (preferably a digital readout) for recordation by a technician or direct analysis by a physician or the subject himself.

Other near-IR apparatus, such as the optical probe and associated instrumentation described in U.S. Pat. No. 4,633,087 (Rosenthal), can be adapted to practice the present methods in which near-IR interactance is used to quantitatively measure blood glucose levels.

This embodiment can utilize a location device specially adapted to permit the user to locate the interactance instrument discussed above accurately along a vein. The location device permits the skin to be marked to ensure that repeated measurements are taken from the same location.

In the lightweight, hand-held interactance analysis instrument 10 illustrated in FIG. 1, included is one or more means for providing at least one point source of near-infrared energy of a predetermined bandwidth of interest which is positioned within a first chamber 30 of the instrument 10. The near-infrared point source means is positioned so that near-infrared energy being emitted from the point source means will be focussed by lens 12 through window 14 and onto the skin of the test subject. The near-infrared point source means may comprise one or a plurality of infrared emitting diodes (IREDs). Two such IREDs 16 are visible in the embodiment illustrated in FIG. 1. In other embodiments employing a plurality of IREDs, three, four or more IREDs may be utilized as the point source means.

Figure 5A:
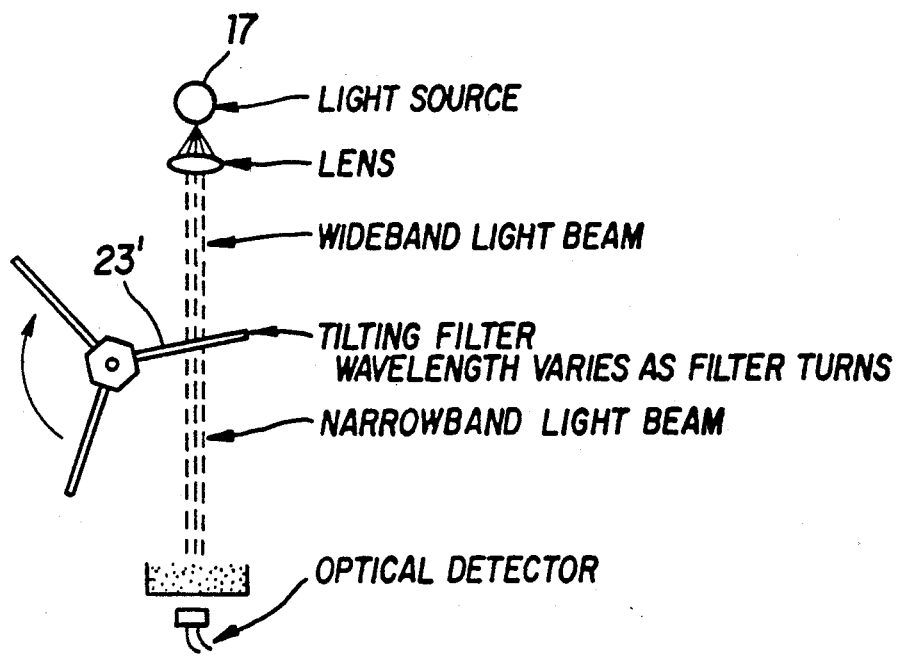
FIGS. 5A and 5B illustrates two known configurations for interposing filters in a light path.
Figure 5B:
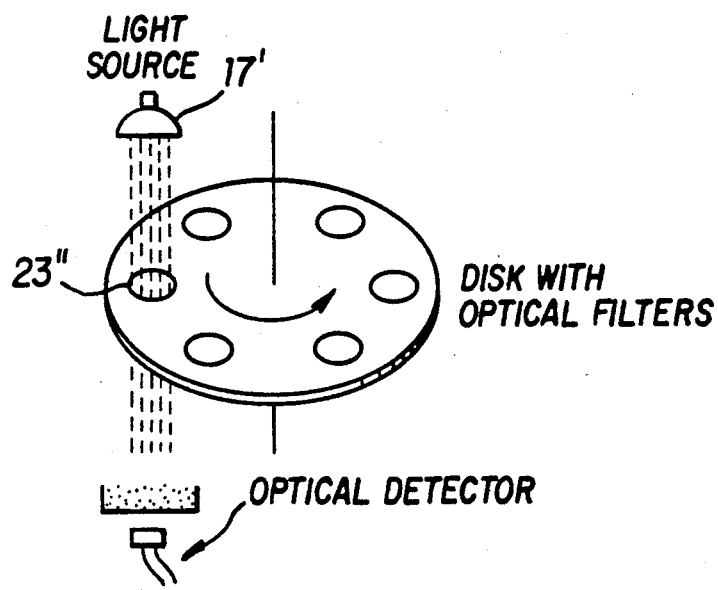

In lieu of laborious characterization and sorting of each IRED, narrow bandpass optical filters (as shown schematically in FIG. 1) can be provided between the infrared emitting diodes and the lens 12. According to this embodiment, a filter 23 is positioned between each IRED and lens 12 for filtering near infrared radiation exiting each IRED and thereby allowing a narrow band of near-infrared radiation of predetermined wavelength to pass through the filter and lens 12. Utilization of narrow bandpass optical filters provides for specific wavelength selection independent of the center wavelengths of the particular infrared emitting diodes being used. Measurements can be taken inside the half power bandwidth of the IREDs, or alternatively, outside the half power bandwidth of the IREDs as disclosed in commonly owned U.S. Pat. No. 4,286,327. FIGS. 5A and 5B illustrate two other known configurations for interposing filters 23, and 23" respectively in a light path. The light source in FIGS. 5A and 5B can be either a light bulb 17 or 17' respectively, or one or more IREDs.

An optical detector, illustrated schematically FIG. 1 and designated by reference numeral 28, is disposed within a lower end portion 42 of a second chamber 40 in case 20. Inner wall 22 is positioned between detector 28 and lens 12, thereby providing an optically-isolating mask which prevents near infrared radiation from the point source means and/or lens 12 from impinging directly on detector 28. A near-infrared optical detector 28 generates an electrical signal when near-infrared radiation is detected thereby.

The optical detector 28 is connected to the input of an electrical signal amplifier 32 by suitable electrical conducting means 33. Amplifier 32 may be an inexpensive integrated circuit (IC) signal amplifier, and amplifies the signals generated when near-IR energy strikes detector 28. The output of amplifier 32 is fed to a controller/data processor and display driver 34 which provides a signal to readout device 36. The readout device 36 may have a digital display for directly displaying the amount of glucose present in the subject's blood.

The embodiment of FIG. 1 includes an optical filter 29 for shielding all but the desired near-IR energy from detector 28. Filter 29 and window 14 are positioned for direct contact with the skin of the test subject. An optically clear window can be employed in lieu of filter 29, if desired.

As noted earlier, the embodiment illustrated in FIG. 1 utilizes the principal of near-IR interactance for quantitative analysis. In interactance, light from a source is shielded by an opaque member from a detector so that only light that has interacted with the subject is detected.

In use, the analysis instrument 10 is positioned so that its flat bottom surface rests on the skin directly above the prominent vein of the wrist of a test subject. Light at the selected wavelengths emerging from the instrument interacts with venous blood of the subject and is detected by detector 28. Detector 28 generates an electrical signal which is processed as described above.

Figure 3:
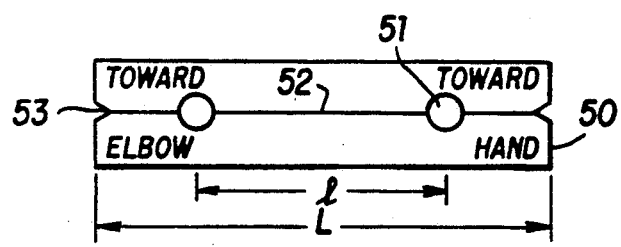
FIG. 3 is an elevational view of a location device for use with the instrument shown in FIG. 1.

Accurate analysis is facilitated when the user locates the transmitter and detector filter (or window) directly over a prominent vein of the wrist. The location device illustrated in FIG. 3 simplifies this procedure. The device 50 is constructed of, e.g., a plastic material and has an overall length L equal to the length L of the analysis instrument 10 of FIG. 1. Two holes 51 are present in the device and are located in the same relation as 14 and 29 in FIG. 1, on midline 52, a distance l apart corresponding to the distance l of FIG. 1. The holes 51 permit observation of the prominent vein. When the device is placed on the wrist and the vein is centered in each hole 51, the wrist is marked (e.g. with a felt-tipped pen) at notches 53. The location device is then removed and replaced by the analysis instrument 10 with assurance that the instrument is properly located over the vein.

Figure 4:
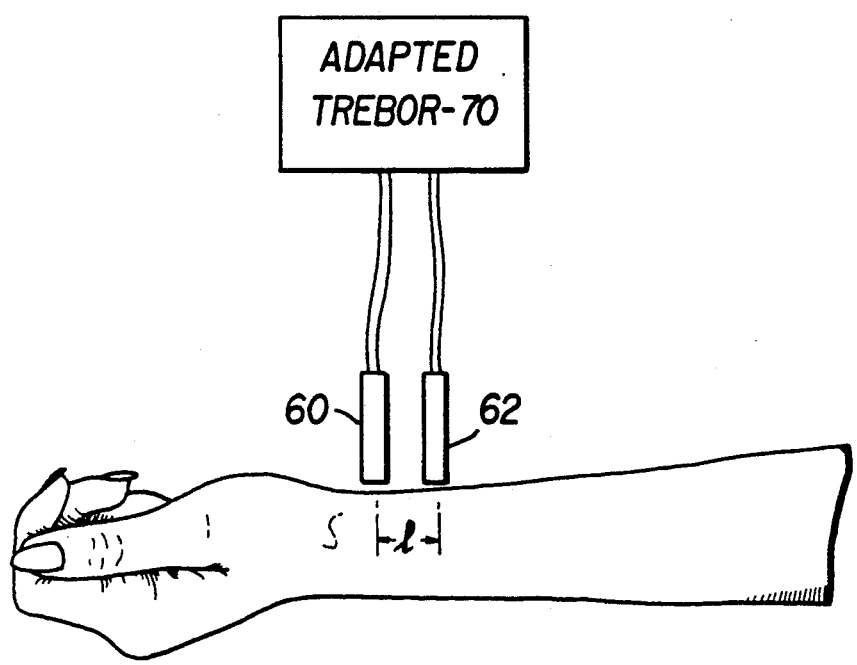
FIG. 4 illustrates one embodiment for practicing the inventive method.

An alternate procedure for practicing the inventive method is accomplished by the use of fiber optic light probes as seen in FIG. 4. These probes are connected with a near-IR analysis instrument such as the commercially available TREBOR-70 scanning spectrophotometer which has been adapted to process a signal for glucose analysis. A probe 60 is placed over the prominent vein and transmits near-IR energy of the desired wavelength(s). The near-IR energy interacts with the blood constituents and is collected by a second probe 62 placed over the vein a short distance l from first probe 60. A detector associated with the analytical instrument provides an electrical signal which is processed, as described above, to reveal quantitative information concerning blood glucose.

We have found that accurate quantitative analysis of blood glucose levels can be made at a variety of wavelengths with both interactance and transmittance technologies. In presently preferred embodiments illustrated in FIGS. 2A and 2B, near-IR light energy is transmitted through the finger of the test subject and then detected by an optical detector. As in the above described embodiments, a combination of measurement wavelengths is selected which emphasizes the glucose absorption and removes the effect of interfering absorption, for example, due to water, fat and protein.

Figure 2A:
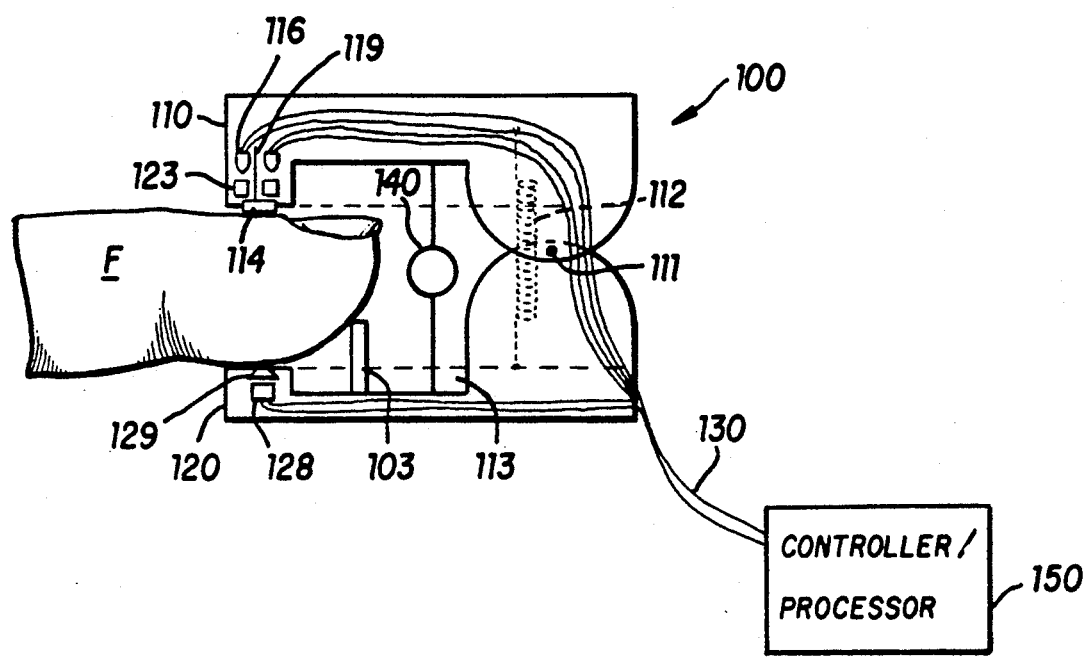
FIGS. 2A and 2B are partially schematic elevational views of alternate embodiments of near-infrared quantitative analysis instruments.

In the embodiment shown in FIG. 2A, a near-IR probe 100 is adapted to be placed over the finger F of a test subject and in this particular embodiment includes a point source means of near-IR light energy comprised of two IREDs 116 disposed within an upper flange 110. Each IRED is paired with a narrow bandpass optical filter 123 and is optically isolated via opaque light baffle 119. The inwardly-facing surface of flange 110 is provided with an optional optically clear window 114 for placement against the subject's finger.

Upper flange 110 is hinged about shaft 111 to lower flange 120, and a spring 112 serves to maintain the flanges in a closed position. An optical detector 128 is disposed in lower flange 120 opposite the near-IR source 116. The detector is disposed behind an optional window 129 which can be constructed of a material which is either optically clear or which excludes visible light yet permits near-IR light to pass. A finger stop 103 helps place and maintain the subject's finger in its proper position within the probe 100. Each of the flanges is provided with light-shielding barriers 113 (shown in phantom in FIG. 2A) to block ambient light from entering the probe.

In this embodiment the IREDs are pulsed, i.e. energized in sequence, so that the detector 128 receives light transmitted from only one of the IREDs at any one time. This pulsed IRED technology is described in commonly owned U.S. Pat. No. 4,286,327 which is incorporated by reference herein. In other similar embodiments a group of IREDs (and optional narrow bandpass filters) with identical wavelength output can be pulsed.

Probe 100 is in electrical connection with a processor unit which is schematically illustrated in FIG. 2A. The processor unit houses a power source, signal amplifying, data processing and display circuitry as described in connection with the embodiment of FIG. 1 and standard in near-IR analysis instrumentation.

Figure 2B:
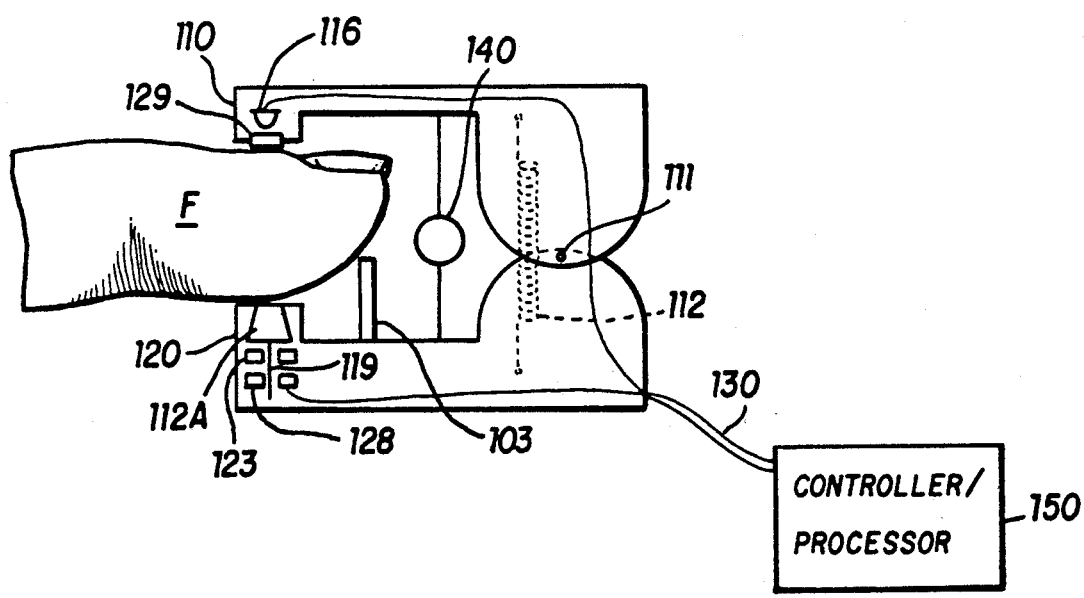

An alternate embodiment is seen in FIG. 2B. Here, probe 110 includes one or more constant output IREDs 116 installed behind an optional window 129. Light transmitted through the finger is gathered by optical funnel 112A, which is constructed of a transparent or translucent material, and detected by multiple detectors 128. The detectors are optically isolated from one another by opaque light baffle 119. Each detector is paired with a narrow bandpass optical filter 123 and thus is set up to detect only light within the narrow wavelength range of its filter.

Near-IR point source means 116 can consist of one or more IREDs of known bandwidth and center frequency output or, as described above, can include a narrow bandpass optical filter within the light path to provide for the detection of only those wavelengths which are of interest. Multiple wavelengths can be utilized in transmission analysis and can be generated via multiple IREDs provided they are consecutively illuminated. Another approach is to use a single IRED with multiple bandpass filters which are mechanically moved through the light path as seen in FIG. 5. A third approach uses a single or group of IREDs capable of emitting a plurality of desired wavelengths with the use of multiple optical filters, each filter being associated with a respective detector. Single IREDs which emit two, three or four narrow bandwidths are commercially available.

In use, the finger of the test subject is inserted between the flanges 110 of the probe 100. Near-IR light energy is emitted by the point source means, is transmitted through the finger and is detected by optical detector 128. The electrical signals produced by the detectors are transmitted via line 130 to a controller/processor unit 150 where the signal is amplified and data processed using a suitable algorithm as described below. Blood glucose level is displayed on a readout device which preferably includes a digital display.

Accurate measurements of the concentration of blood glucose ca be made using near-IR quantitative analysis algorithms which have only a single variable term, such as the following:

Approximated First Derivative Algorithm $$C = K_0 + K_1 [\log 1/I_G - \log 1/I_H]$$

Approximated Second Derivative Algorithm $$C = K_0 + K_1 [\log 1/I_A - 2^*\log 1/I_B + \log 1/I_C]$$

Normalized First Derivative Algorithm $$C = K_0 + K_1 \frac{[\log 1/I_G - \log 1/I_H]}{[\log 1/I_X - \log 1/I_J]}$$

Figure 6:
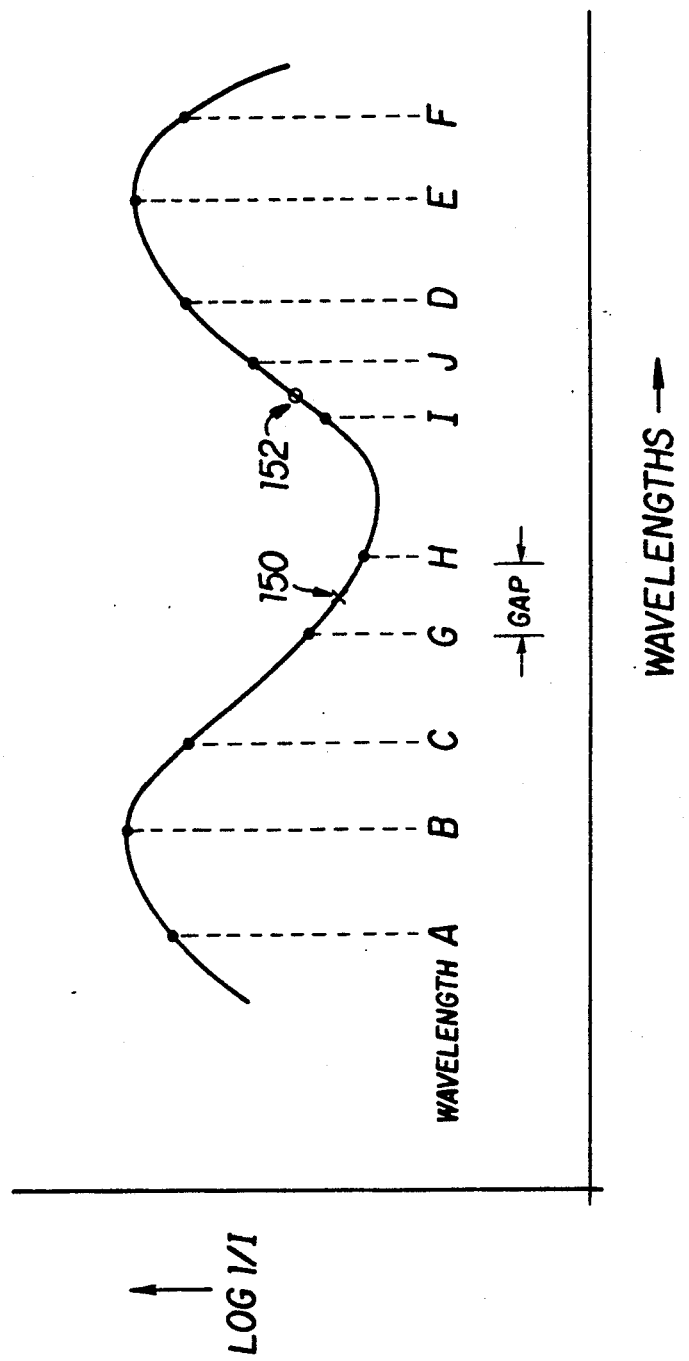
FIG. 6 is a plot of log (1/I) versus wavelength.

Normalized Second Derivative Algorithm $$C = K_0 + K_1 \frac{[\log 1/I_A - 2^*\log 1/I_B + \log 1/I_C]}{[\log 1/I_D - 2^*\log 1/I_E + \log 1/I_F]}$$

where C denotes concentration of glucose present in the blood, $K_0$ is the intercept constant, $K_1$ is the line slope of the variable term, and the log 1/I terms each represent an Optical Density (O.D.) value at a particular wavelength. In FIG. 6, an example of an overall absorbance curve for a test subject is shown, wherein log 1/I (O.D.) values for the above algorithms are plotted. In FIG. 6, optical energy is absorbed at wavelength B proportional to the constituent being measured, and optical energy is absorbed at wavelength E proportional to the total substance being measured. Points 150 and 152 are first derivative midpoints. The distance between, for example, wavelength G and wavelength H is referred to herein as the "gap" between two wavelengths. It has been found that a plurality of wavelength pairs, all centered on the same wavelength (approximately 980 nm), can be used in the above algorithms. These algorithms are easily programmed into suitable microprocessor circuitry by those skilled in the art. The use of these single variable term equations is highly desirable because it allows simplified instrument calibration, thereby allowing the production of low cost instruments.

The intercept constant $K_0$ and the slope constant $K_1$ are initially determined for a "master unit" (which employs components similar or identical to those of the production units) by simple linear regression analyses of known samples, i.e., optical readings are obtained from the instrument being constructed for a representative number of samples which have been previously accurately analyzed via another, well-established technique, and the optical readings and previously measured percentages are utilized to calculate sets of calibration constants for blood glucose content using a conventional regression algorithm in a digital computer. The respective $K_1$ slope and $K_0$ intercept values are then programmed into each production unit of the analyzing instrument so that each production unit can directly compute values for blood glucose from optical data readings.

Another class of usable near-IR standard algorithms involves the use of multiple regression terms. Such terms can be individual log 1/I terms or can be a multiple number of first or second derivative terms with or without a normalizing denominator. Such multiple terms may provide additional accuracy, but introduce much higher calibration expense which results in a more expensive instrument.

Data on a plurality of physical parameters of the test subject can also be utilized in conjunction with multiple wavelength measurement of near-infrared interactance, as in prior U.S. Pat. No. 4,633,087, to improve the accuracy of the present blood glucose measurements.

Selection of combinations of wavelengths which emphasize glucose absorption and removes possible interfering absorptions can be performed by computer search studies. In general, a suitable combination of wavelengths will include at least one wavelength which is sensitive to blood glucose, and at least one wavelength which is insensitive to blood glucose (reference wavelength). The following examples show results of wavelength search studies, which are provided herein for illustrative purposes only, and are not to be construed in a limiting sense.

EXAMPLE I

Figure 7:
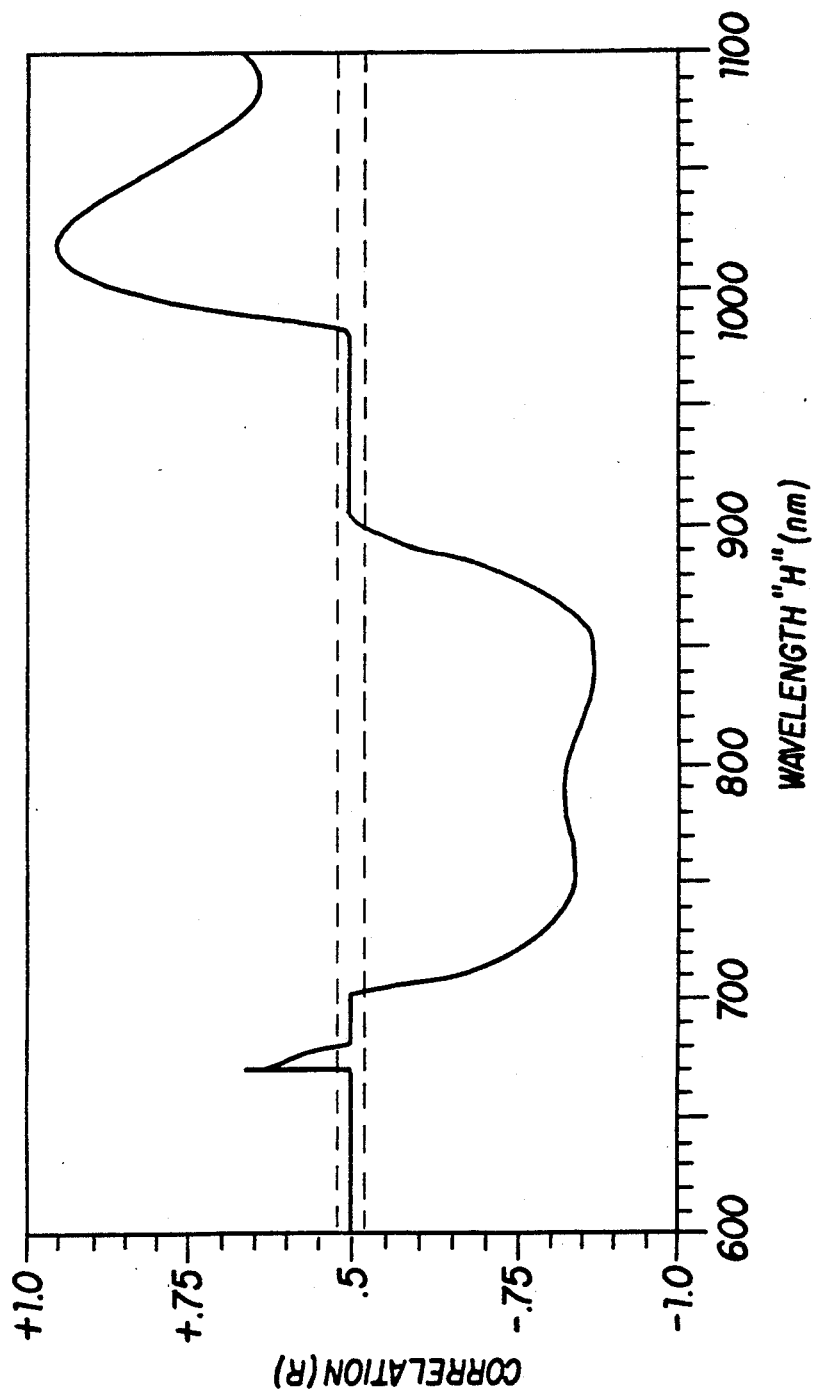
FIG. 7 illustrates a wavelength search study via a plot of correlation coefficient versus wavelength.

FIG. 7 presents correlation coefficient versus wavelength data from a search study utilizing an approximated first derivative algorithm as defined above, and illustrates that the use of the wavelength pair of 980± (plus and minus) 35 nm provides a high correlation between blood glucose and absorption of near-IR energy at those two wavelengths. FIG. 7 utilizes the above approximated first derivative algorithm, wherein G and H are as shown in FIG. 6, and equal to 945 nm and 1015 nm respectively. Thus, in this example, the "gap" is 70 nm (1015 nm-945 nm). The number of samples tested was 30 in this case. The value for $K_0$ in the approximated first derivative algorithm is 196.9 and for $K_1$ is 4,802.6. In this case, the standard deviation was 13.54, with a correlation of +0.948. Reference numeral 154 of FIG. 7 indicates a range of candidates for wavelength H with a "gap" equal to 70 nm and a "smoothing" factor of 41. "Smoothing" is the modification of data derived from a scanning spectrophotometer in order to simulate the results which would be obtained at the half power bandwidth of optical filters. "Smoothing" involves taking data at an equal number of wavelengths above and below the bandwidth of interest and averaging the results. Thus, with a "smoothing" value of 41, data is taken at 20 wavelengths above and 20 wavelengths below the bandwidth of interest, in addition to the bandwidth of interest. An example of one embodiment of the invention uses IREDs which provide near-IR energy at two frequencies which are, respectively, equidistant above and below approximately 980 nm, i.e., they can be represented by the formula 980±x nm. The value of x is not critical so long as the two frequencies are centered on approximately 980 nm. A suitable value for x can be, for example, a number from 10 to 40.

EXAMPLE II

Figure 8:
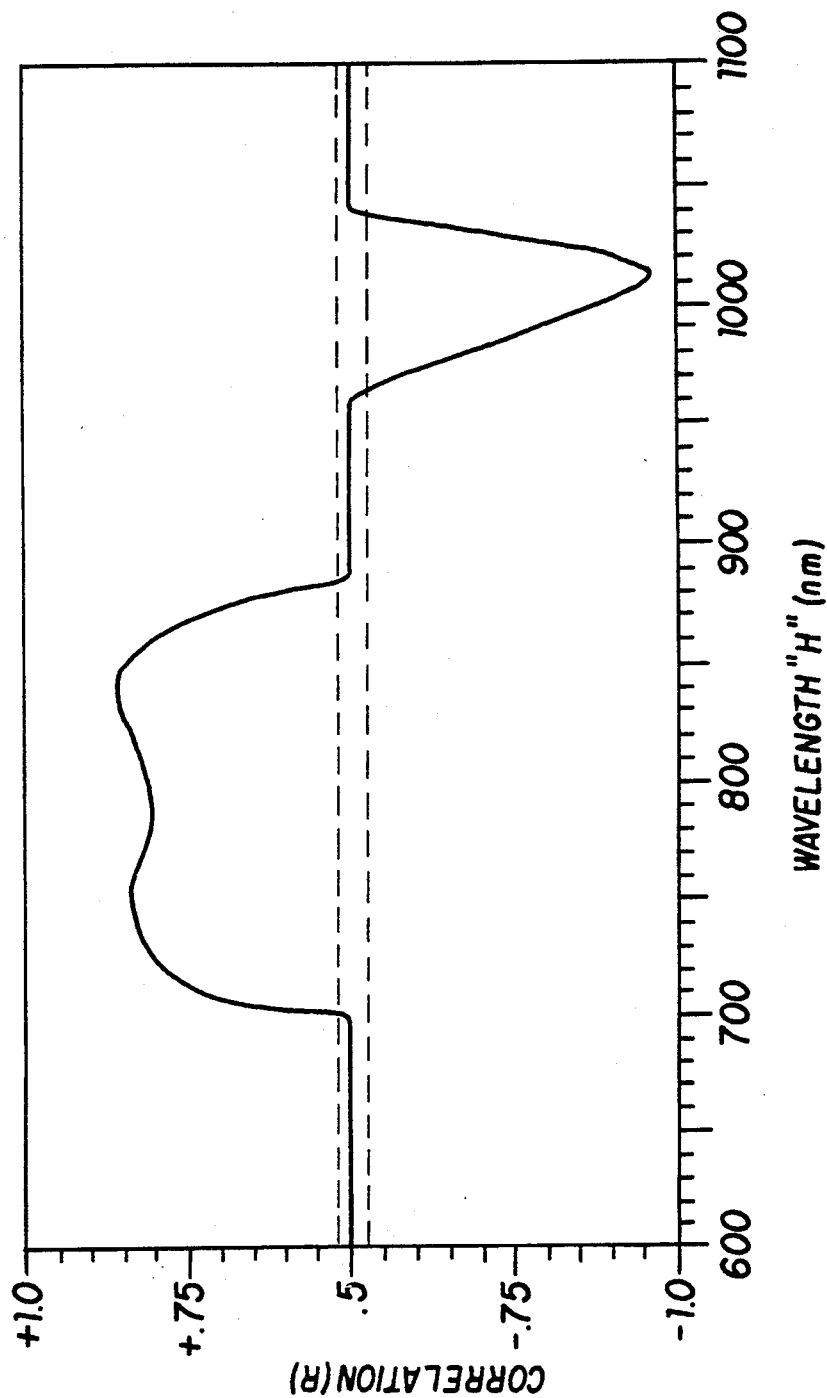
FIGS. 8 and 9 illustrate plots of correlation coefficient versus wavelength for first derivative equations.

FIG. 8 shows that a suitable wavelength for a numerator in the above normalized first derivative algorithm is approximately 1013 nm (i.e., 980 nm + 35 nm) wherein $K_0=296.8$, $K_1=-175.6$, "gap" G-H: 70 nm, wavelength J: 915 nm, "gap" I-J: 20 nm, standard deviation = 12.21 and correlation = -0.958 (30 samples).

EXAMPLE III

Figure 9:
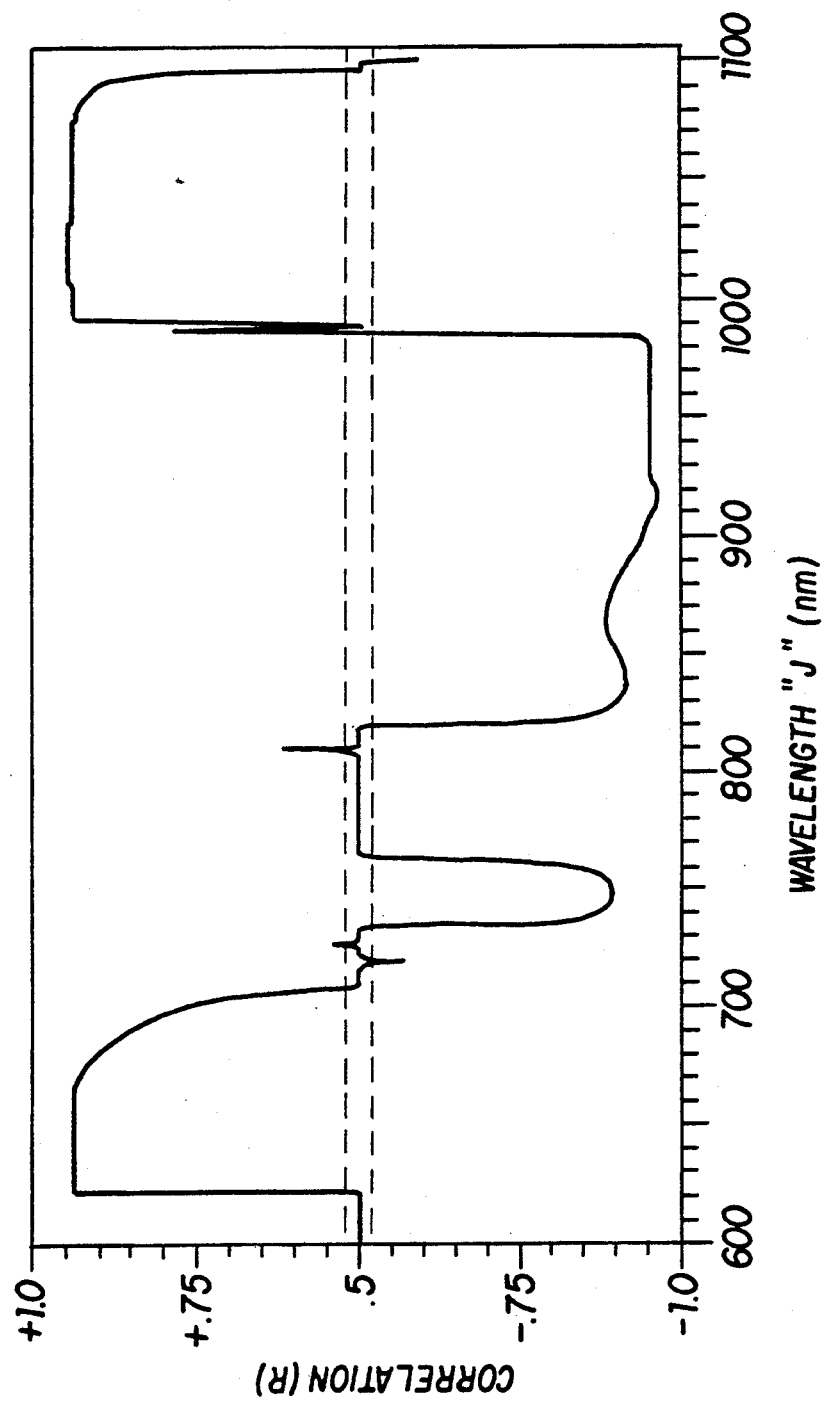

FIG. 9 shows that there are many wavelength regions that can provide midpoint wavelengths for use in the denominator of the above normalized first derivative algorithm when the numerator utilizes 980±35 nm wavelengths, wherein $K_0$, $K_1$, "gap" G-H, gap I-J, standard deviation, correlation and sample size are the same as in Example II and FIG. 8, and wherein wavelength H is 1013 nm. Examples of such wavelength regions are seen to be from 610 to 660 nm, from 910 to 980 nm and from 990 to 1080 nm.

EXAMPLE IV AND V

Figure 10:
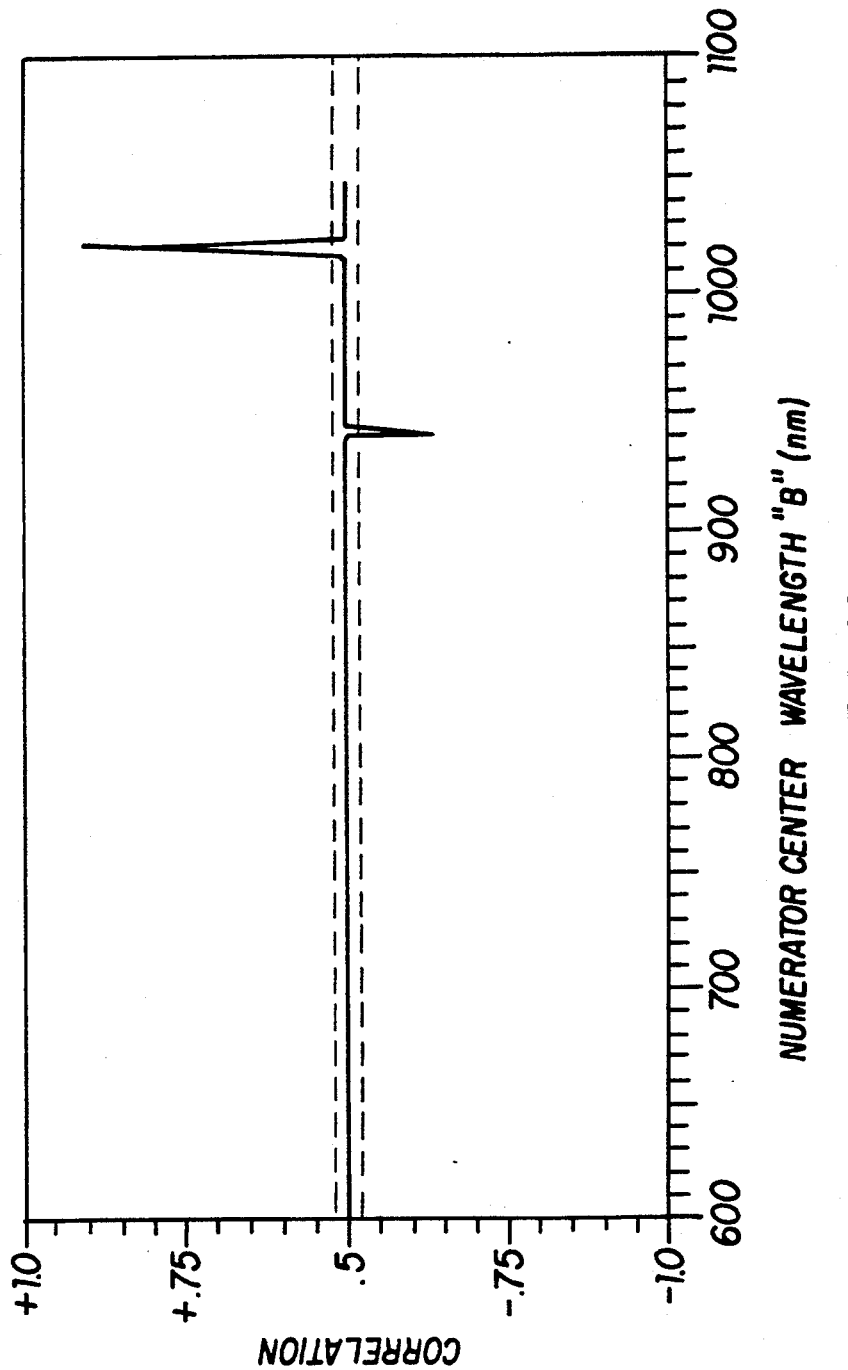
FIGS. 10 and 11 illustrate plots of correlation coefficient versus wavelength for second derivative equations.
Figure 11:
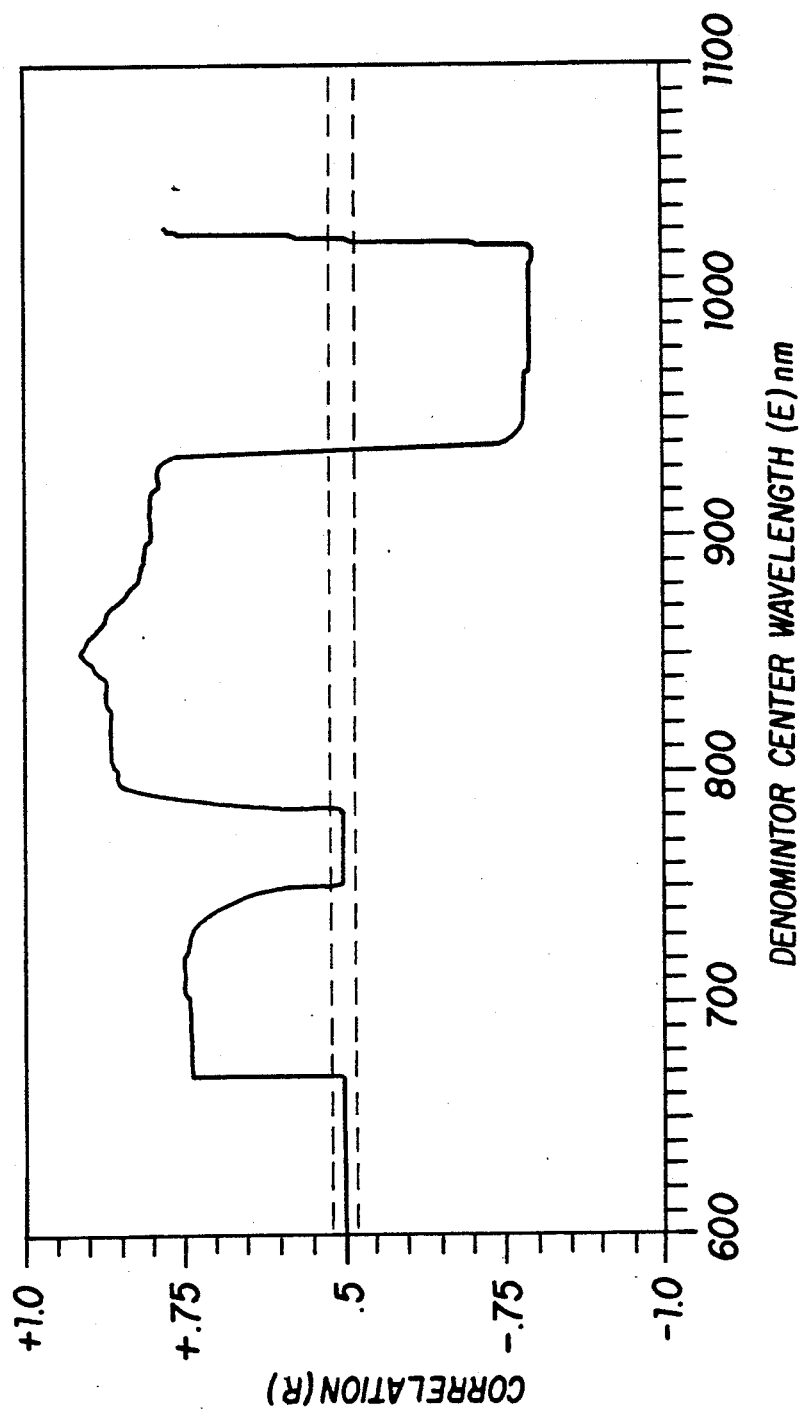

FIGS. 10 and 11 illustrate suitable center wavelengths for use in the normalized second derivative algorithm described above. FIG. 10 is a plot of correlation coefficient versus wavelength which shows that a suitable numerator center frequency is approximately 1020 nm, wherein in the above normalized second derivative algorithm, $K_0=205.856$, $K_1=356.457$, "gap" A-B-C: 53 nm, wavelength E: 850 nm, "gap" D-E-F: 68 nm and standard deviation = 20.44 (47 samples). FIG. 11 shows that a denominator center frequency of about 850 nm is suitable, wherein $K_0$, $K_1$, "gap" A-B-C, "gap" D-E-F, standard deviation, and sample size are as in FIG. 10, and wherein wavelength B is 1020 nm.

The accuracy of the preferred near-IR transmission embodiments shown in FIGS. 2A and 2B can be further improved by altering the algorithm to include finger thickness as a parameter. According to Lambert's law, energy absorption is approximately proportional to the square of the thickness of the object. The thickness of the test subject's finger can be quantified by installing a potentiometer 140 between the flanges of the probe 100 as seen in FIGS. 2A and 2B. The output of the potentiometer, which is in electrical connection with the data processing circuitry, is indicative of finger thickness. A non-linear potentiometer can approximate the $T^2$ value via its output alone, so that a separate squaring calculation step is not required.

Although the invention has been described in connection with certain preferred embodiments, it is not limited to them. Modifications within the scope of the following claims will be apparent to those skilled in the art. For example, accurate measurements can be obtained from parts of the body besides the wrist and the finger. The algorithm used to calculate blood constituent concentration(s) can be altered in accordance with known near-infrared analytical techniques.

We claim:

1. A near-infrared quantitative analysis instrument for non-invasive measurement of blood glucose in blood present in a body part of a subject, comprising:
   (a) means for introducing near-infrared energy into blood present in a body part of a subject;
   (b) a near-infrared detector for detecting near-infrared energy within the range of about 600 to 1110 nanometers emerging from the body part and for providing a signal upon detection of near-infrared energy within said range emerging from the body part;
   (c) means for positioning both the near-infrared introducing means and the near-infrared detector closely adjacent to the body part so that near-infrared energy detected by the detector corresponds to blood glucose level in said body part; and
   (d) means for processing the signal produced by the detector into a second signal indicative of the quantity of glucose present in the blood of the subject.

2. An analysis instrument of claim 1 further including means for preventing near-infrared energy from the introducing means from impinging directly on the detector.

3. An analysis instrument of claim 2 wherein said introducing means includes a near-infrared energy source and transmitting means for transmitting said energy into the body part.

4. An analysis instrument of claim 3 wherein said source comprises at least one infrared emitting diode.

5. An analysis instrument of claim 3 wherein said transmitting means comprises a lens for focusing said energy onto the body part.

6. An analysis instrument of claim 2 wherein said processing means comprises amplifier means for amplifying the signal provided by said detector, and data processing means for converting the signal from the detector into said second signal.

7. An analysis instrument of claim 1 wherein said introducing means includes a near infrared source and a filter for selectively transmitting near-infrared energy which filter is disposed between said source and said body part.

8. An analysis instrument of claim 7 for blood glucose measurement wherein said filter selectively transmits near-infrared energy of between about 600 and about 1100 nanometers.

9. An analysis instrument of claim 1 wherein said introducing means provides a bandwidth centered on about 980 nanometers.

10. An analysis instrument of claim 1 wherein said positioning means includes means for marking a position for said instrument over a blood vessel of a subject.

11. An analysis instrument of claim 1 wherein said positioning means comprises means for positioning said introducing means closely adjacent to one side of the body part and for positioning said detector closely adjacent to a generally opposite side of the body part so that near-IR energy emitted by the introducing means is transmitted through said body part and detected by said detector.

12. An analysis instrument of claim 11 wherein the positioning means positions the introducing means and the detector on opposite sides of a finger.

13. An analysis instrument of claim 12 further including means for measuring the thickness of the body part and for providing a signal indicative of the thickness of the body part.

14. An analysis instrument of claim 13 wherein said means for providing a signal comprises a variable resistor.

15. An analysis instrument of claim 11 wherein said introducing means comprises at least one infrared emitting diode.

16. An analysis instrument of claim 11 wherein said introducing means provides a bandwidth centered on about 980 nanometers.

17. An analysis instrument of claim 11 wherein said introducing means includes a near infrared source and a filter for selectively transmitting near-infrared energy which filter is disposed between said source and said body part.

18. An analysis instrument of claim 17 for blood glucose measurement wherein said filter selectively transmits near-infrared energy of between about 600 and about 1100 nanometers.

19. The analysis instrument of claim 11 further including at least one filter for selectively transmitting near-infrared energy, which filter is disposed between the detector and said body part.

20. An analysis instrument of claim 19 for blood glucose measurement wherein said filter selectively transmits near-infrared energy of between about 600 and about 1100 nanometers.

21. The method of claim 21 wherein near infrared energy centered on about 980 nanometers is introduced into the blood within said body part.

22. The analysis instrument of claim 1 wherein said introducing means provides at least one wavelength pair centered on about 980 nanometers.

23. The analysis instrument of claim 1 wherein the signal processing means processes the signal according to the formula $$C = K_0 + K_1[\log 1/I_G - \log 1/I_H]$$

wherein C is a concentration of glucose present in the blood, $K_0$ is an intercept constant, $K_1$ is line slope of $$[\log 1/I_G - \log 1/I_H]$$

and $\log 1/I_G$ and $\log 1/I_H$ each represent an optical density value a corresponding wavelengths G and H.

24. The analysis instrument of claim 1 wherein the signal processing means processes the signal according to the formula $$C = K_0 + K_1[\log 1/I_A - 2^*\log 1/I_B + \log 1/I_C]$$

wherein C is a concentration of glucose present in the blood, $K_0$ is an intercept constant, $K_1$ is line slope of $$[\log 1/I_A - 2^*\log 1/I_B + \log 1/I_C]$$

and $\log 1/I_A$, $\log 1/I_B$, and $\log 1/I_C$ each represent an optical density value at corresponding wavelengths A, B and C.

25. The analysis instrument of claim 1 wherein the signal processing means processes the signal according to the formula $$C = K_0 + K_1 \frac{[\log 1/I_G - \log 1/I_H]}{[\log 1/I_I - \log 1/I_J]}$$

wherein C is a concentration of glucose present in the blood, $K_0$ is an intercept constant, $K_1$ is line slope of $$\frac{[\log 1/I_G - \log 1/I_H]}{[\log 1/I_I - \log 1/I_J]}$$

and $\log 1/I_G$, $\log 1/I_H$, $\log 1/I_I$ and $\log 1/I_J$ each represent an optical density value at corresponding wavelengths G, H, I and J.

26. The analysis instrument of claim 1 wherein the signal processing means processes the signal according to the formula $$C = K_0 + K_1 \frac{[\log 1/I_A - 2^*\log 1/I_B + \log 1/I_C]}{[\log 1/I_D - 2^*\log 1/I_E + \log 1/I_F]}$$

wherein C is concentration of glucose present in the blood, $K_0$ is an intercept constant, $K_1$ is line slope of $$\frac{[\log 1/I_A - 2^*\log 1/I_B + \log 1/I_C]}{[\log 1/I_D - 2^*\log 1/I_E + \log 1/I_F]}$$

and $\log 1/I_A$, $\log 1/I_B$, $\log 1/I_C$, $\log 1/I_D$, $\log 1/I_E$, and $\log 1/I_F$ each represent an optical density value at corresponding wavelengths A, B, C, D, E and F.

27. A non-invasive method for quantitatively analyzing blood glucose in blood of a subject, comprising:
(a) introducing at least one pair of wavelengths of near-infrared energy into blood within a body part of the subject, said pair being centered on a wavelength within the range of about 600 to 1100 nanometers;

(b) detecting near-infrared energy emerging from the subject with a detector which provides a signal upon detecting energy emerging from the subject, and (c) processing the signal to provide a second signal indicative of the amount of glucose present in the blood of the subject.

28. The method of claim 27 wherein at least one pair of wavelengths of near infra-red energy centered on about 980 nanometers is introduced into the blood within said body part.

29. The method of claim 27 wherein the signal is processed according to the formula $$C = K_0 + K_1[\log 1/I_G - \log 1/I_H]$$

wherein C is a concentration of glucose present in the blood, $K_0$ is an intercept constant, $K_1$ is line slope of $$[\log 1/I_G - \log 1/I_H]$$

and $\log 1/I_G$ and $\log 1/I_H$ each represent an optical density value at corresponding wavelengths G and H.

30. The method of claim 27 wherein the signal processing means processes the signal according to the formula $$C = K_0 + K_1[\log 1/I_A - 2^*\log 1/I_B + \log 1/I_C]$$

wherein C is concentration of glucose present in the blood, $K_0$ is an intercept constant, $K_1$ is line slope of $$[\log 1/I_A - 2^*\log 1/I_B + \log 1/I_C]$$

and $\log 1/I_A$, $\log 1/I_B$, and $\log 1/I_C$ each represent an optical density value at corresponding wavelengths A, B and C.

31. The method of claim 27 wherein the signal processing means processes the signal according to the formula $$C = K_0 + K_1 \frac{[\log 1/I_G - \log 1/I_H]}{[\log 1/I_I - \log 1/I_J]}$$

wherein C is concentration of glucose present in the blood, $K_0$ is an intercept constant, $K_1$ is line slope of $$\frac{[\log 1/I_G - \log 1/I_H]}{[\log 1/I_I - \log 1/I_J]}$$

and $\log 1/I_G$, $\log 1/I_H$, $\log 1/I_I$ and $\log 1/I_J$ each represent an optical density value at corresponding wavelengths G, H, I and J.

32. The method of claim 27 wherein the signal processing means processes the signal according to the formula $$C = K_0 + K_1 \frac{[\log 1/I_A - 2^*\log 1/I_B + \log 1/I_C]}{[\log 1/I_D - 2^*\log 1/I_E + \log 1/I_F]}$$

wherein C is concentration of glucose present in the blood, $K_0$ is an intercept constant, $K_1$ is line slope of $$\frac{[\log 1/I_A - 2^*\log 1/I_B + \log 1/I_C]}{[\log 1/I_D - 2^*\log 1/I_E + \log 1/I_F]}$$

and $\log 1/I_A$, $\log 1/I_B$, $\log 1/I_C$, $\log 1/I_D$, $\log 1/I_E$, and $\log 1/I_F$ each represent an optical density value at corresponding wavelengths A, B, C, D, E and F.

* * * * *

UNITED STATES PATENT AND TRADEMARK OFFICE
CERTIFICATE OF CORRECTION

PATENT NO. : 5,028,787
DATED : July 2, 1991
INVENTOR(S) : Rosenthal et al.

It is certified that error appears in the above-identified patent and that said Letters Patent is hereby corrected as shown below:

Title page,
Item [56], References Cited,
U.S. Patent 4,975,581 12/1990 Robison et al., submitted on 1449 but not on cover; and "4,863,530" should be -- 4,663,530 --.

OTHER PUBLICATIONS,
"Infratec New" should be -- Infratec - A New --; and "Ne-lcor" should be -- Nellcor --.

Column 2,
Line 7, "content" should be -- content. --.
Line 12, "Chemists" should be -- Chemists. --.

Column 3,
Line 48, "illustrates" should be -- illustrate --.

Column 5,
Line 10, "focussed" should be -- focused --.

Column 7,
Line 61, "ca" should be -- can --.

Column 8,
Line 7, "log $1/I_x$" should be -- log $1/I_I$ --.

UNITED STATES PATENT AND TRADEMARK OFFICE
CERTIFICATE OF CORRECTION

PATENT NO. : 5,028,787
DATED : July 2, 1991
INVENTOR(S) : Rosenthal et al.

It is certified that error appears in the above-identified patent and that said Letters Patent is hereby corrected as shown below:

Column 11, claim 21,
Line 66, (23 in application as filed), "claim 21" should be -- claim 27 --.

Signed and Sealed this

Twelfth Day of March, 2002

Attest:

JAMES E. ROGAN
Attesting Officer      Director of the United States Patent and Trademark Office